(12) United States Patent
Wang et al.

(10) Patent No.: US 10,501,509 B2
(45) Date of Patent: Dec. 10, 2019

(54) METHOD OF PREPARING FUNCTIONAL PEPTIDES FROM GERMINATED BEANS

(71) Applicant: Zhejiang Academy of Agricultural Sciences, Hangzhou, Zhejiang (CN)

(72) Inventors: Wei Wang, Zhejiang (CN); Nan Wang, Zhejiang (CN); Yu Zhang, Zhejiang (CN); Junhong Wang, Zhejiang (CN); Zuoyi Zhu, Zhejiang (CN); Xue Li, Zhejiang (CN); Jiahong Zhu, Zhejiang (CN)

(73) Assignee: Zhejiang Academy of Agricultural Sciences, Hangzhou (CN)

( * ) Notice: Subject to any disclaimer, the term of this patent is extended or adjusted under 35 U.S.C. 154(b) by 306 days.

(21) Appl. No.: 15/404,154

(22) Filed: Jan. 11, 2017

(65) Prior Publication Data

US 2017/0291926 A1    Oct. 12, 2017

Related U.S. Application Data

(63) Continuation of application No. PCT/CN2016/081550, filed on May 10, 2016.

(30) Foreign Application Priority Data

Apr. 11, 2016 (CN) .......................... 2016 1 0221298

(51) Int. Cl.
*C07K 14/415* (2006.01)

(52) U.S. Cl.
CPC ................................. *C07K 14/415* (2013.01)

(58) Field of Classification Search
CPC .............................. C07K 14/415; C12P 21/06
See application file for complete search history.

(56) References Cited

FOREIGN PATENT DOCUMENTS

| CN | 101238904 A | 8/2008 |
|----|-------------|--------|
| CN | 101658298 A | 3/2010 |

OTHER PUBLICATIONS

International Search Report of PCT Patent Application No. PCT/CN2016/081550 dated Dec. 12, 2016.

*Primary Examiner* — Lisa J Hobbs

(57) ABSTRACT

The present invention discloses a method of preparing a functional peptide from a germinated bean, including the steps of: germinating a bean until a sprout length is about 0.5-1.0 cm; adding water to the obtained germinated bean, and then blending and crushing the germinated bean; adjusting the obtained slurry to a pH value between 6.5-8.0, and then adding neutral protease, papain and compound flavor protease to perform enzymatic reaction under stirring condition, wherein an enzymatic reaction solution is obtained including the functional peptide; subjecting the enzymatic reaction solution to ultrafiltration using an ultrafiltration membrane; keeping the ultrafiltrated enzymatic reaction solution at a temperature between 70-80° C. or using ozonated water at a concentration between 20-25 mg/L thereby avoiding decomposition by microorganisms; and performing spray drying to obtain the functional peptide.

4 Claims, No Drawings

METHOD OF PREPARING FUNCTIONAL PEPTIDES FROM GERMINATED BEANS

CROSS REFERENCE TO RELATED APPLICATIONS

This application is a continuation application of PCT application No. PCT/CN2016/081550 filed on May 10, 2016, which claims priority to Chinese patent application No. 201610221298.8 filed on Apr. 11, 2016, the entire contents of which are incorporated herein by reference.

FIELD OF TECHNOLOGY

The present invention relates to the technical field of bioengineering, in particular to a method of preparing functional peptides from germinated beans such as soybeans.

BACKGROUND

In recent years, with an accelerated rhythm of life and an enhanced living standard, people are more and more inclined to various health foods. Beans and sprouts, being rich in nutrients and health ingredients, are becoming a hot topic of lifestyle. Bean seeds not only are rich in proteins, fats, cellulose, hemicellulose, pectin, mannan, bean gum, soluble fibers, etc, but also contain certain bioactive substances which are beneficial to human health. However, there are also multiple anti-nutritional factors such as tannin, phytic acid and protease inhibitors present in bean seeds, which to a certain extent limit the utilization of the nutrients in beans. Upon germination, the anti-nutritional factors in bean seeds are degraded, and nutrients contained in bean seeds such as carbohydrates, proteins and fats are decomposed into small molecular compounds which facilitate digestion and absorption. The contents of health functional components such as saponin, vitamins, polypeptides, flavonoids, phenols, soy isoflavones, levodopa and γ-aminobutyric acid also increase significantly.

"Beans" usually refers to seeds of leguminous crops in agricultural production which possess a certain market demand and a relatively large-scale production, and may be used as bean sprouts and raw materials for cultivating seedlings. These include soybeans or soya beans, mung beans, broad beans, peanuts, Alfalfa, lentils and the like for producing bean sprouts, and peas, grass peas, broad beans, adzuki beans and the like for cultivating seedlings.

By extracting nutritious, bioactive functional peptides from natural proteins and applying these functional peptides to health food and fortified nutritional food, not only may the high quality proteins in food and food processing be fully utilized, but also the added values of the protein raw materials from a wide range of source may be effectively increased. Meanwhile, this also greatly enhances the technological content of traditional food.

At the present time, there are relative more reports on the preparation of bioactive peptides from food proteins. The technology of preparing functional peptides by using bean raw materials at germination stage as the protein source is not yet available.

SUMMARY

The technical problem sought to be solved by the present invention is to provide an effective low-cost method of preparing functional peptides from germinated beans.

In order to solve the above technical problem, the present invention provides a method of preparing a functional peptide from a germinated bean, including the following steps:

(1) germinating a bean to obtain a germinated bean (i.e., a sprouting whole bean) with a sprout length of 0.5-1.0 cm;

(2) adding water to the germinated bean obtained from step (1), and then blending and crushing the germinated bean to obtain a slurry, wherein the germinated bean and the water are in a weight ratio of 1:0.9-1.1 (preferably 1:1);

(3) adjusting the slurry obtained from step (2) to a pH value between 6.5-8.0 (preferably 7-7.5), and then adding neutral protease, papain and compound flavor protease to perform enzymatic reaction under stirring condition at a temperature between 50-55° C. for 2.5-3.5 hours (preferably 3 hours), wherein an enzymatic reaction solution is obtained including the functional peptide;

wherein the neutral protease and the germinated bean obtained from step (1) are in a weight ratio of 0.9-1.1% (preferably 1%), the papain and the germinated bean obtained from step (1) are in a weight ratio of 0.9-1.1% (preferably 1%), and the compound flavor protease and the germinated bean obtained from step (1) are in a weight ratio of 0.9-1.1% (preferably 1%).

In a preferred embodiment of the method of preparing a functional peptide from a germinated bean, the method further includes:

(4) subjecting the enzymatic reaction solution obtained from step (3) to ultrafiltration using an ultrafiltration membrane at an operating pressure between 0.1-0.2 MPa and an operating temperature between 20-45° C. to obtain an ultrafiltrated enzymatic reaction solution, wherein the ultrafiltration membrane has a molecular weight cut-off of 5 kDa;

(5) keeping the ultrafiltrated enzymatic reaction solution (i.e., the enzymatic reaction peptide solution with a molecular weight of less than 5 kDa) at a temperature between 70-80° C. (preferably 75° C.) or adding ozonated water at a concentration between 20-25 mg/L thereby avoiding decomposition by microorganisms (also includes anti-browning reaction); and (6) performing spray drying to obtain the functional peptide (in powder form).

Remarks:

The above ultrafiltrated enzymatic reaction solution is kept at the temperature between 70-80° C. (preferably 75° C.) up until the spray drying is completed. Generally, 160-180 L of ozonated water is used for every 200 kg of germinated beans.

In a preferred embodiment of the method of preparing a functional peptide from a germinated bean, in step (3), when time of the enzymatic reaction is up, the enzymatic reaction solution is heated (heating rate at 8-12° C./min) to a temperature between 85-98° C. (preferably 90° C.) and kept at the temperature for 10-15 minutes, and then cooled (cooling rate at 8-12° C./min) to room temperature to terminate the enzymatic reaction, and then centrifuged (at 2500-3500 r/min for 15-25 minutes, preferably at 3000 r/min for 20 minutes), wherein a supernatant of the centrifugation is the enzymatic reaction solution including the functional peptide.

In a preferred embodiment of the method of preparing a functional peptide from a germinated bean, inlet air of the spray drying is controlled at a temperature between 180-190° C. and outlet air of the spraying drying is controlled at a temperature between 95-110° C.

In a preferred embodiment of the method of preparing a functional peptide from a germinated bean, the neutral protease has an enzyme activity of 500,000 U/kg, the papain has an enzyme activity of 3,500,000 U/g and the compound flavor protease has an enzyme activity of 1000 LAPU/g.

In a preferred embodiment of the method of preparing a functional peptide from a germinated bean, the bean is soybean.

In step (2) of the present invention, NaOH solution at a concentration of 0.5 M or HCl solution at a concentration of 0.5 M is used to perform adjustment of the pH value.

In the present application, "room temperature" generally refers to 10-30° C.

The inventors of the present invention have discovered that nutrients are most abundant and vitality is most vigorous at the germination stage of beans (a sprout length of 0.5-1.0 cm). When the sprout length exceeds 1 cm, the nutrients in beans are gradually converted and consumed. Therefore, at the germination stage of beans, the proteins are activated by bioactive enzymes and various biological functions of the organisms may be shown. It is the optimal choice to use the germinated beans at this stage as the raw materials of proteins in the preparation of bioactive peptides.

The method of preparing functional peptides from germinated beans according to the present invention has the following advantages:

(1) The functional peptides prepared by the present invention are obtained by subjecting germinated beans with a sprout length of 0.5-1.0 cm to hydrolysis by compound biological enzymes. The functional peptides possess inhibitory activities against HMG-CoA reductase, ACE enzyme and α-glucosidase, and adjuvant therapeutic effects on patients with hyperlipoidemia, hypertension and hyperglycemia. The functional peptides are safe and free of toxic side effect, may play a role in health care of individuals with blood lipid level, and have no influence on normal blood lipid level.

(2) The raw materials used in the present invention are widely available and low in price. With the technical conversion by the present invention, the added values of bean products can be effectively increased. The present invention is of great significance for continuing the promotion of quality improvement in agriculture.

(3) The products of the present invention may be used as medicine, health food, food, food additive, drug synergist and the like. The process is scientific and reasonable, easy to operate and has strong industrial applicability.

DETAILED DESCRIPTION

Example 1

A method of preparing functional peptides from germinated soybeans, carried out according to the following steps:

Germination of soybeans was carried out in the conventional way. 100 kg of germinated beans with a sprout length of about 0.5 cm were weighed. 100 kg of water was added and the germinated beans were crushed, blended and thoroughly stirred. The obtained slurry was first adjusted to a pH value of 7.0, and then 1 kg of neutral proteases (500,000 U/kg), 1 kg of papain (3,500,000 U/g) and 1 kg of compound flavor proteases (1000 LAPU/g) were added. Enzymatic reaction was carried out for 3 hours at 50-55° C.

When time was up, the enzymatic reaction products were rapidly heated to 90° C. (heating rate at 10° C./min) and kept at the temperature for 10 minutes, and then rapidly cooled to room temperature (cooling rate at 10° C./min) to terminate the reaction. Thereafter, the enzymatic reaction products were centrifuged in a J-6M High-Capacity Refrigerated Centrifuge (Beckman Coulter, Inc.) at 3000 r/min for 20 minutes at 4° C. 150 kg of supernatant was obtained, being the enzymatic solution (the enzymatic solution contained germinated soybean functional peptides).

The enzymatic solution was subjected to ultrafiltration using an ultrafiltration membrane at an operating pressure of 0.1-0.2 MPa and an operating temperature of 20-45° C. to obtain an ultrafiltrated enzymatic solution. The molecular weight cut-off of the ultrafiltration membrane was 5 kDa. The enzymatic peptide solution, having a molecular weight of less than 5 kDa, was kept warm at 75° C. until spraying was completed. Thereafter, spray drying was carried out (parameters of the spray drying process: temperature of inlet air controlled at 180° C., temperature of outlet air controlled at 95° C.). 15.5 kg of germinated soybean functional peptide powder was obtained, having a peptide content of 90.2% and a product yield of 15.5%. The product appeared in a delicate white color and had a pure balanced flavor.

The germinated soybean functional peptide powder was dissolved at a concentration of 1.0 mg/ml. The inhibitory activity of the functional peptide against HMG-CoA reductase was measured by HPLC (Wei Wang, Acta Agriculturae Zhejiangensis, 2015), and the measured $IC_{50}$ was 0.75 mg/ml. The inhibitory activity $IC_{50}$ against ACE enzyme was 0.56 mg/ml. The inhibitory activity $IC_{50}$ against α-glucosidase was 0.95 mg/ml.

Example 2

A method of preparing functional peptides from germinated soybeans, carried out according to the following steps:

Germination of soybeans was carried out in the conventional way. 200 kg of germinated beans with a sprout length of about 0.5 cm were weighed. 200 kg of water was added and the germinated beans were crushed, blended and thoroughly stirred. The obtained slurry was first adjusted to a pH value of 7.5, and then 2 kg of neutral proteases (500,000 U/kg), 2 kg of papain (3,500,000 U/g) and 2 kg of compound flavor proteases (1000 LAPU/g) were added. Enzymatic reaction was carried out for 3 hours at 50-55° C.

When time was up, the enzymatic reaction products were rapidly heated to 90° C. (heating rate at 10° C./min) and kept at the temperature for 10 minutes, and then rapidly cooled to room temperature (cooling rate at 10° C./min) to terminate the reaction. Thereafter, the enzymatic reaction products were centrifuged in a J-6M High-Capacity Refrigerated Centrifuge (Beckman Coulter, Inc.) at 3000 r/min for 20 minutes at 4° C. The obtained supernatant was the enzymatic solution (the enzymatic solution contained germinated soybean functional peptides).

The enzymatic solution was subjected to ultrafiltration using an ultrafiltration membrane at an operating pressure of 0.1-0.2 MPa and an operating temperature of 20-45° C. to obtain an ultrafiltrated enzymatic solution. The molecular weight cut-off of the ultrafiltration membrane was 5 kDa. The enzymatic peptide solution, having a molecular weight of less than 5 kDa, was filled in a 500 L laminated insulation tank and 170 L of ozonated water at 20 mg/L was added into the tank. Thereafter, spray drying was carried out (parameters of the spray drying process: temperature of inlet air controlled at 190° C., temperature of outlet air controlled at 100° C.). 32.5 kg of germinated soybean functional peptide powder was obtained, having a peptide content of 92.8% and a product yield of 16.25%. The product appeared in a delicate white color, and had a pure balanced flavor and a slight smell of frankincense.

The germinated soybean functional peptide powder was dissolved at a concentration of 1.0 mg/ml. The inhibitory activity of the functional peptide against HMG-CoA reductase was measured by HPLC (Wei Wang, Acta Agriculturae Zhejiangensis, 2015), and the measured $IC_{50}$ was 0.85 mg/ml. The inhibitory activity $IC_{50}$ against ACE enzyme was 0.60 mg/ml. The inhibitory activity $IC_{50}$ against α-glucosidase was 0.91 mg/ml.

Comparative Example 1-1

The sprout length of about 0.5 cm in Example 1 was changed to 1.5 cm. The rest were the same as Example 1.

Comparative Example 1-2

The sprout length of about 0.5 cm in Example 1 was changed to 0.2 cm. The rest were the same as Example 1.

Comparative Example 2-1

The use of neutral proteases was abolished. The amounts of papain and compound flavor proteases were changed from 1 kg to 1.5 kg. The rest were the same as Example 1.

Comparative Example 2-2

The use of papain was abolished. The amounts of neutral proteases and compound flavor proteases were changed from 1 kg to 1.5 kg. The rest were the same as Example 1.

Comparative Example 2-3

The use of compound flavor proteases was abolished. The amounts of neutral proteases and papain were changed from 1 kg to 1.5 kg. The rest were the same as Example 1.

Data on the product yields and the inhibitory activities of the germinated soybean functional peptide powder dissolved at a concentration of 1.0 mg/ml obtained from the above Comparative Examples are shown in Table 1 below.

TABLE 1

|  | Product Yield (%) | Inhibitory Activity $IC_{50}$ against HMG-CoA Reductase (mg/ml) | Inhibitory Activity $IC_{50}$ against ACE Enzyme (mg/ml) | Inhibitory Activity $IC_{50}$ against α-glucosidase (mg/ml) |
| --- | --- | --- | --- | --- |
| Example 1 | 15.5 | 0.75 | 0.56 | 0.95 |
| Comparative Example 1-1 | 13.1 | 1.35 | 2.13 | 3.63 |
| Comparative Example 1-2 | 12.1 | 1.47 | 2.08 | 1.39 |
| Comparative Example 2-1 | 14.0 | 1.23 | 1.89 | 2.61 |
| Comparative Example 2-2 | 14.8 | 1.08 | 1.06 | 2.13 |
| Comparative Example 2-3 | 13.6 | 1.32 | 1.25 | 2.34 |

Lastly, it should also be noted that the above description has only exemplified a few specific embodiments of the present invention. It is apparent that the present invention is not limited to the above embodiments but may also include various modifications. All modifications which may be directly derived from or associated with the disclosure of the present invention by one skilled in the art are considered to be within the protected scope of the present invention.

What is claimed is:

1. A method of preparing a functional peptide from a germinated bean, comprising the following steps:
   (1) germinating a bean to obtain a germinated bean with a sprout length of 0.5-1.0 cm;
   (2) adding water to the germinated bean obtained from step (1), and then blending and crushing the germinated bean to obtain a slurry, wherein the germinated bean and the water are in a weight ratio of 1:0.9-1.1;
   (3) adjusting the slurry obtained from step (2) to a pH value between 6.5-8.0, and then adding neutral protease, papain and compound flavor protease to incubate under stirring condition at a temperature between 50-55° C. for 2.5-3.5 hours to obtain an enzymatic reaction solution comprising the functional peptide;
   wherein the neutral protease and the germinated bean obtained from step (1) are in a weight ratio of 1:10, the papain and the germinated bean obtained from step (1) are in a weight ratio of 1:10, and the compound flavor protease and the germinated bean obtained from step (1) are in a weight ratio of 1:10;
   (4) heating the enzymatic reaction solution obtained from step (3) to a temperature between 85-98° C. and keeping the enzymatic reaction solution at the temperature for 10-15 minutes, and then cooling the heated enzymatic reaction solution to a room temperature to terminate the enzymatic reaction, and then centrifuging the cooled enzymatic reaction solution at 2500-3500 r/min for 15-25 minutes, wherein a supernatant of the centrifugation contains the functional peptide;
   (5) subjecting the supernatant obtained from step (4) to ultrafiltration using an ultrafiltration membrane at an operating pressure between 0.1-0.2 MPa and an operating temperature between 20-45° C. to obtain an ultrafiltrated solution, wherein the ultrafiltration membrane has a molecular weight cut-off of 5 kDa;
   (6) keeping the ultrafiltrated solution at a temperature between 70-80° C.; and
   (7) performing spray drying to obtain the functional peptide.

2. The method according to claim 1, wherein inlet air of the spray drying is controlled at a temperature between 180-190° C. and outlet air of the spraying drying is controlled at a temperature between 95-110° C.

3. The method of claim 1, wherein the neutral protease has an enzyme activity of 500,000 u/kg, the papain has an enzyme activity of 3,500,000 u/g and the compound flavor protease has an enzyme activity of 1000 LAPU/g.

4. The method of claim 1, wherein the bean is soybean.

* * * * *